(12) United States Patent
Schader et al.

(10) Patent No.: US 10,918,804 B2
(45) Date of Patent: Feb. 16, 2021

(54) MEDICAMENT INJECTION DEVICE WITH SPRING-ASSISTED PROTECTIVE NEEDLE CAP

(71) Applicant: Sanofi-Aventis Deutschland GmbH, Frankfurt am Main (DE)

(72) Inventors: Marc Schader, Frankfurt am Main (DE); Michael Helmer, Frankfurt am Main (DE); Peter Nober, Rommersheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 332 days.

(21) Appl. No.: 15/778,781

(22) PCT Filed: Nov. 21, 2016

(86) PCT No.: PCT/EP2016/078264
§ 371 (c)(1),
(2) Date: May 24, 2018

(87) PCT Pub. No.: WO2017/089275
PCT Pub. Date: Jun. 1, 2017

(65) Prior Publication Data
US 2018/0369498 A1 Dec. 27, 2018

(30) Foreign Application Priority Data
Nov. 27, 2015 (EP) .................... 15196695

(51) Int. Cl.
*A61M 5/32* (2006.01)
*A61M 5/28* (2006.01)
(Continued)

(52) U.S. Cl.
CPC ........ *A61M 5/3204* (2013.01); *A61M 5/2033* (2013.01); *A61M 5/2455* (2013.01);
(Continued)

(58) Field of Classification Search
CPC .............. A61M 5/3204; A61M 5/3202; A61M 5/3243; A61M 5/2455; A61M 5/3213;
(Continued)

(56) References Cited

U.S. PATENT DOCUMENTS 4,725,267 A * 2/1988 Vaillancourt ....... A61M 5/3202
604/192
4,976,701 A 12/1990 Ejlersen et al.
(Continued)

FOREIGN PATENT DOCUMENTS

| CN | 1181645 | 5/1998 |
|---|---|---|
| CN | 101072595 | 11/2007 |

(Continued)

OTHER PUBLICATIONS

International Search Report and Written Opinion in International Application No. PCT/EP2016/078264, dated Feb. 20, 2017, 12 pages.
(Continued)

*Primary Examiner* — Bhisma Mehta
*Assistant Examiner* — Rachel T. Smith
(74) *Attorney, Agent, or Firm* — Fish & Richardson P.C.

(57) ABSTRACT

A medicament injection device including: a main body; a medicament cartridge holder fixed with respect to the main body, wherein the medicament cartridge holder is configured to hold a medicament cartridge; a needle carrier carrying a needle, wherein the needle carrier is axially movable with respect to the main body; and a rotatable cap at a distal end of the device, wherein the cap includes a first pre-stressed spring coupled to the needle carrier, wherein the cap is arranged so that rotational movement thereof causes release of the first pre-stressed spring thereby causing the needle carrier to move axially towards a proximal end of the device.

20 Claims, 4 Drawing Sheets

(51) Int. Cl.
*A61M 5/24* (2006.01)
*A61M 5/20* (2006.01)

(52) U.S. Cl.
CPC ........ *A61M 5/2459* (2013.01); *A61M 5/2466* (2013.01); *A61M 5/286* (2013.01); *A61M 5/3202* (2013.01); *A61M 5/3213* (2013.01); *A61M 5/3243* (2013.01); *A61M 2005/2403* (2013.01); *A61M 2005/2474* (2013.01)

(58) Field of Classification Search
CPC .................. A61M 5/343; A61M 5/344; A61M 2005/2474
See application file for complete search history.

(56) References Cited

U.S. PATENT DOCUMENTS

2013/0331794 A1* 12/2013 Ekman ................ A61M 5/3204
604/197

2015/0196718 A1* 7/2015 Radmer .............. A61M 5/3202
604/192

FOREIGN PATENT DOCUMENTS

| | | |
|---|---|---|
| CN | 101180090 | 5/2008 |
| CN | 103269730 | 8/2013 |
| WO | WO 96/30065 | 10/1996 |
| WO | WO 2006/063124 | 6/2006 |
| WO | WO 2015/140262 | 9/2015 |

OTHER PUBLICATIONS

International Preliminary Report on Patentability in International Application No. PCT/EP2016/078264, dated May 29, 2018, 9 pages.

* cited by examiner

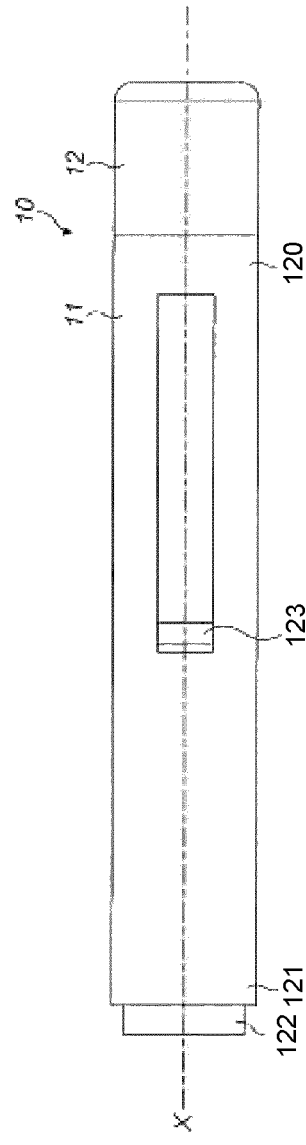
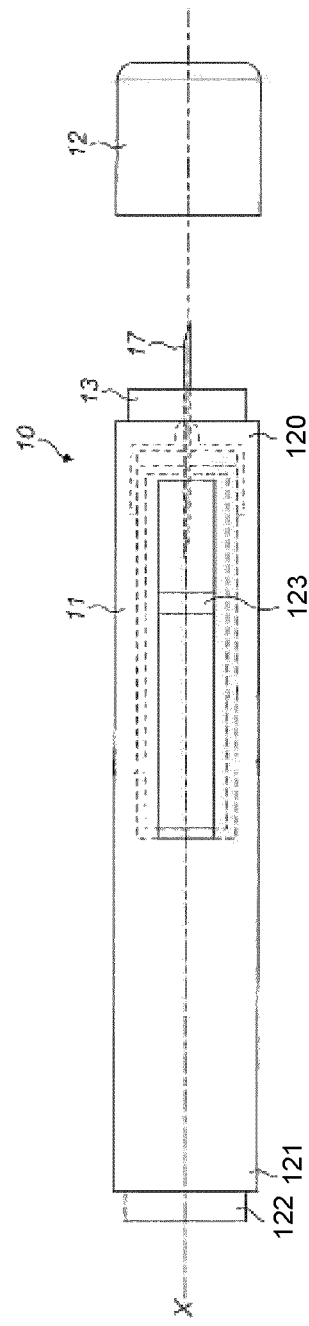

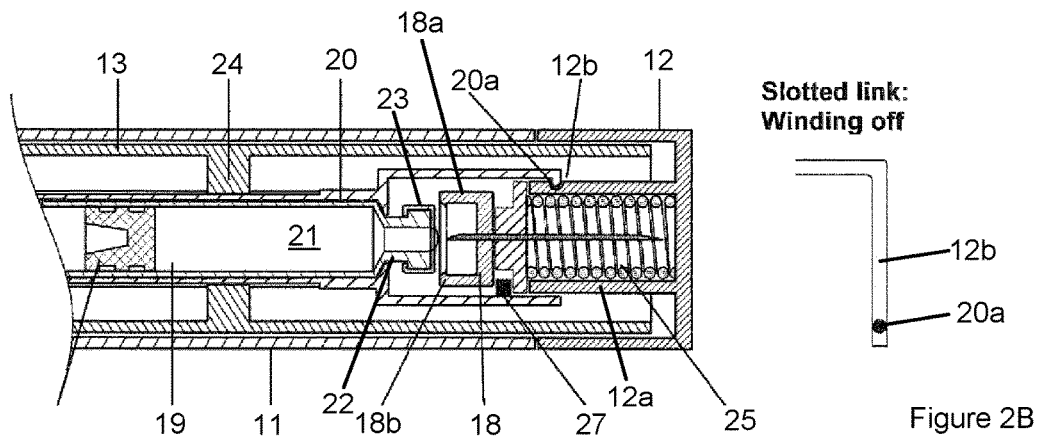
Figure 2A
Figure 2B
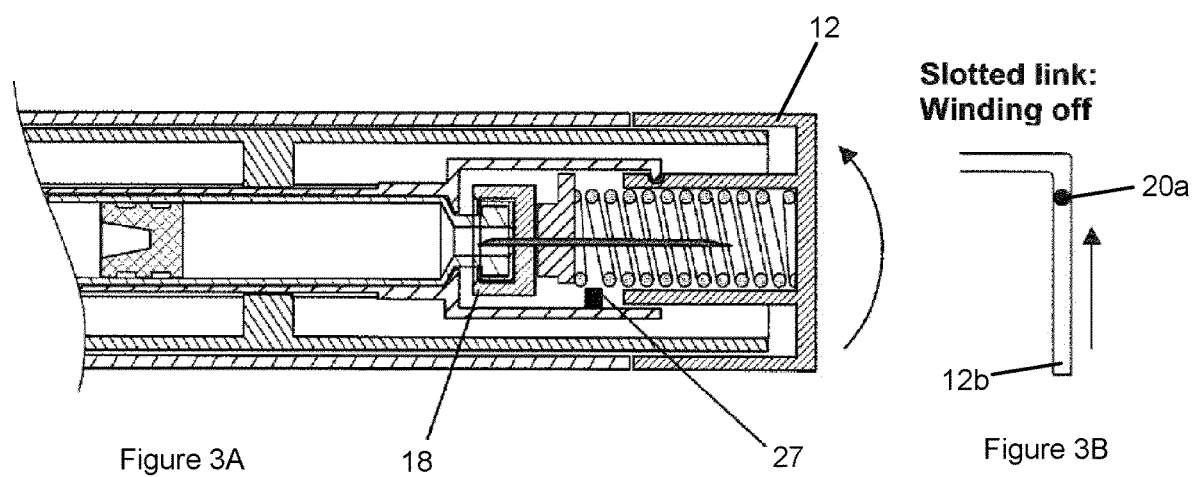
Figure 3A
Figure 3B

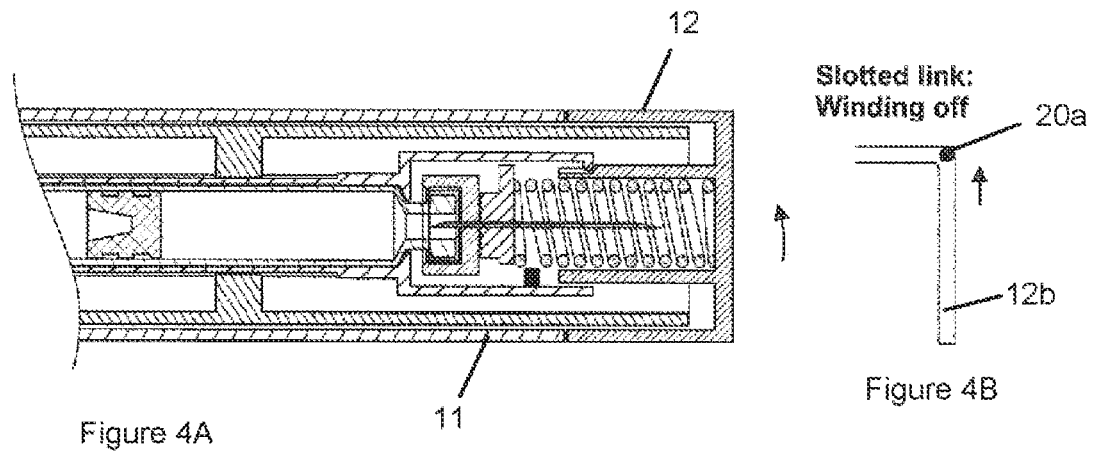
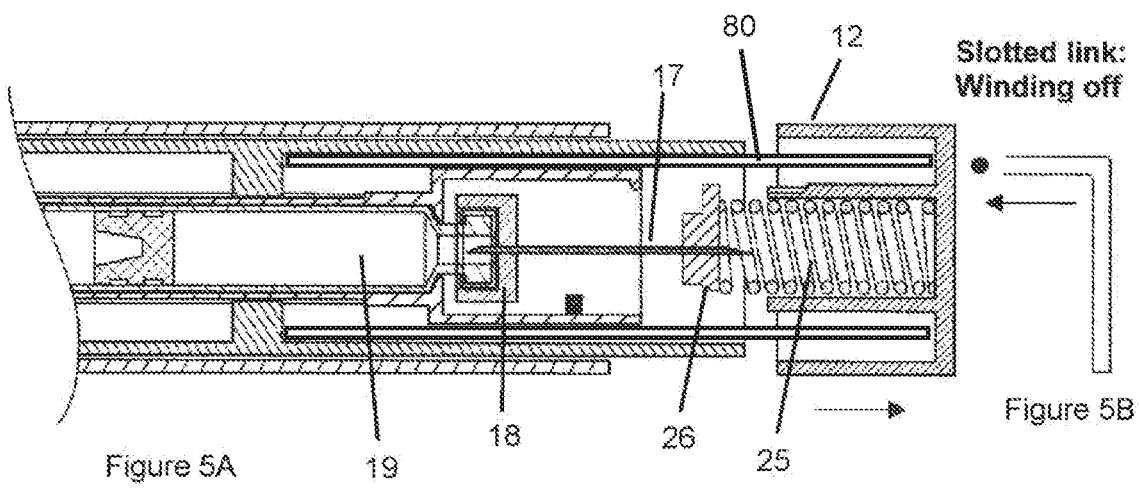

MEDICAMENT INJECTION DEVICE WITH SPRING-ASSISTED PROTECTIVE NEEDLE CAP

CROSS REFERENCE TO RELATED APPLICATIONS

This application is a U.S. national stage application under 35 USC § 371 of International Patent Application No. PCT/EP2016/078264, filed on Nov. 21, 2016, which claims priority to European Patent Application No. 15196695.9, filed on Nov. 27, 2015, the entire contents of each of which are incorporated herein by reference.

TECHNICAL FIELD

The disclosure generally relates to a medicament injection device.

BACKGROUND

Medicament injection devices can take various forms. One form uses a syringe, where medicament is stored in a hollow cylinder, typically formed of glass. The medicament is sealed from the environment with a plunger moveable within the cylinder, and a needle fluidly connected to the syringe's distal end. The needle must remain capped in order to maintain the medicament under sterile conditions.

Another form of injection device uses a cartridge instead of a syringe, the cartridge having a distal seal instead of the syringe's needle. Typically, a patient connects a double-ended needle to the cartridge before injection, thereby piercing the cartridge's seal with the proximal tip of the double-ended needle.

While a cartridge can provide handling and storage advantages relative to syringes, they are not without shortcomings. For example, the attachment of a needle to the cartridge requires an additional step. This step can be problematic for patients with limited dexterity, poor coordination, or who have lost a degree of sensation in their hands. Even with such disadvantages, in certain situations it is desirable to provide an injection device in which the needle is kept separate from the medicament until such time as the patient wishes to commence the injection.

SUMMARY

A first embodiment provides a medicament injection device comprising: a main body; a medicament cartridge holder fixed with respect to the main body, wherein the medicament cartridge holder is configured to hold a medicament cartridge; a needle carrier carrying a needle, wherein the needle carrier is axially movable with respect to the main body; a rotatable cap at a distal end of the device, wherein the cap comprises a first pre-stressed spring coupled to the needle carrier, and at least one activation element and wherein the first pre-stressed spring is attached at a proximal end thereof to a plate, and wherein rotation of the cap causes the plate and the first pre-stressed spring to be released, thereby causing the plate to push the needle holder towards a proximal end of the device.

The plate may have at least one indent located along the circumferential surface thereof arranged to allow respective at least one activation element to pass therethrough when the indent and the activation element are in rotational alignment.

The device may further comprise a second pre-stressed spring arranged to be released in response to rotation of the cap subsequent to release of the first pre-stressed spring, thereby causing the cap to move axially away from the main body in a distal direction.

The cap may comprise a tubular needle shielding element.

The device may further comprise a guide element and a cooperating groove, wherein one of the guide element and a cooperating groove is disposed in the cap and the other of the guide element and a cooperating groove is disposed in the remainder of the device so that the cap is prevented from being removed until the cap is rotationally aligned with the guide element.

The cap may comprise a tubular needle shielding element. The guide element may depend from the medicament cartridge holder for engagement with the cap, and the groove may be provided on the outer surface of the tubular needle shielding element to receive the guide element.

The groove may comprise a circumferential part and an axial part.

The groove may comprise a portion that is relatively narrow in comparison to the remainder of the groove.

The needle holder may be arranged to become fixed to the medicament cartridge.

The needle holder may comprise a lip arranged to cooperate with a head of the medicament cartridge.

The first spring may be a helical spring or a wave spring.

The medicament cartridge holder contains a medicament cartridge having a penetrable barrier at a distal end thereof, and the axial movement of the needle carrier towards the proximal end may cause the needle to pierce the barrier of the medicament cartridge.

The medicament cartridge may contain a medicament.

A second embodiment provides a method of operating a medicament injection device having a rotatable cap, the method comprising rotating the rotatable cap, thereby causing release of a first pre-stressed spring thereby causing a needle carrier to move axially towards a proximal end of the device.

BRIEF DESCRIPTION OF THE DRAWINGS

Exemplary embodiments are described with reference to the accompanying drawings, in which:

FIGS. 1A and 1B are side-on views of an auto-injector device according to certain embodiments;

FIG. 2A is a side-on cross sectional schematic view of a device having a cap before the cap is rotated;

FIG. 2B is a representation of the engagement of the guide element with the slotted link in the device shown in FIG. 2A;

FIGS. 3A and 4A are side-on cross sectional schematic views of the device of the second embodiment as the cap is being removed;

FIGS. 3B and 4B are representations of the engagement of the guide element with the slotted link in the device shown in FIGS. 3A and 4A, respectively;

FIG. 5A is a side-on cross sectional schematic view of the device of the second embodiment as the cap is being removed;

FIG. 5B is a representation of the engagement of the guide element with the slotted link in the device shown in FIG. 5A;

DETAILED DESCRIPTION

Figure 6A:
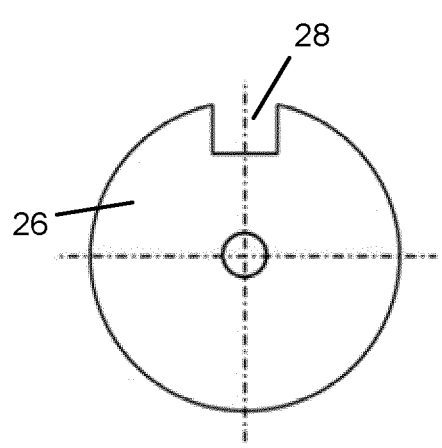
FIG. 6A and FIG. 6B show a frontal view of a plate in accordance with respective embodiments.

Embodiments provide a mechanism for inserting the needle of an injection device such as an auto-injector or syringe into a medicament cartridge containing the medicament to be injected. Providing such a mechanism allows the medicament cartridge to be sealed until such time as the user wishes to commence the injection. Providing an automated mechanism for inserting the needle into the medicament cartridge also reduces the amount of handling of the needle by the user prior to the injection. Indeed, in embodiments the user does not need to touch the needle during the steps of inserting the needle into the medicament cartridge and subsequently actuating the injection of the medicament.

Embodiments provide a mechanism whereby a needle holder holding a needle is automatically connected to a medicament cartridge in response to rotation of a device cap.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or pertain to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device. The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a main body 11 which typically contains a reservoir containing the medicament to be injected (e.g., a syringe) and the components required to facilitate one or more steps of the delivery process. Device 10 can also include a cap assembly 12 that can be detachably mounted to the main body 11. Typically, a user must remove cap 12 from main body 11 before device 10 can be operated.

As shown, main body 11 is substantially cylindrical and has a substantially constant diameter along the longitudinal axis X. The main body 11 has a distal region 120 and a proximal region 121. The term "distal" refers to a location that is relatively closer to a site of injection, and the term "proximal" refers to a location that is relatively further away from the injection site.

Device 10 can also include a needle sleeve 13 coupled to main body 11 to permit movement of sleeve 13 relative to main body 11. For example, sleeve 13 can move in a longitudinal direction parallel to longitudinal axis X. Specifically, movement of sleeve 13 in a proximal direction can permit a needle 17 to extend from distal region 120 of main body 11.

Insertion of needle 17 can occur via several mechanisms. For example, needle 17 may be fixedly located relative to main body 11 and initially be located within an extended needle sleeve 13. Proximal movement of sleeve 13 by placing a distal end of sleeve 13 against a patient's body and moving main body 11 in a distal direction will uncover the distal end of needle 17. Such relative movement allows the distal end of needle 17 to extend into the patient's body. Such insertion is termed "manual" insertion as needle 17 is manually inserted via the patient's manual movement of main body 11 relative to sleeve 13.

Another form of insertion is "automated," whereby needle 17 moves relative to main body 11. Such insertion can be triggered by movement of sleeve 13 or by another form of activation, such as, for example, a button 122. As shown in FIGS. 1A & 1B, button 122 is located at a proximal end of main body 11. However, in other embodiments, button 122 could be located on a side of main body 11.

Other manual or automated features can include drug injection or needle retraction, or both. Injection is the process by which a bung or piston 123 is moved from a proximal location within a syringe (not shown) to a more distal location within the syringe in order to force a medicament from the syringe through needle 17. In some embodiments, a drive spring (not shown) is under compression before device 10 is activated. A proximal end of the drive spring can be fixed within proximal region 121 of main body 11, and a distal end of the drive spring can be configured to apply a compressive force to a proximal surface of piston 123. Following activation, at least part of the energy stored in the drive spring can be applied to the proximal surface of piston 123. This compressive force can act on piston 123 to move it in a distal direction. Such distal movement acts to compress the liquid medicament within the syringe, forcing it out of needle 17.

Following injection, needle 17 can be retracted within sleeve 13 or main body 11. Retraction can occur when sleeve 13 moves distally as a user removes device 10 from a patient's body. This can occur as needle 17 remains fixedly located relative to main body 11. Once a distal end of sleeve 13 has moved past a distal end of needle 17, and needle 17 is covered, sleeve 13 can be locked. Such locking can include locking any proximal movement of sleeve 13 relative to main body 11.

Another form of needle retraction can occur if needle 17 is moved relative to main body 11. Such movement can occur if the syringe within main body 11 is moved in a proximal direction relative to main body 11. This proximal movement can be achieved by using a retraction spring (not shown), located in distal region 120. A compressed retraction spring, when activated, can supply sufficient force to the syringe to move it in a proximal direction. Following sufficient retraction, any relative movement between needle 17 and main body 11 can be locked with a locking mechanism. In addition, button 122 or other components of device 10 can be locked as required.

The cap 12 has an end wall and a curved side wall and a tubular wall 12a extending from the end wall. The cap 12 fits over the needle sleeve 13. The cap 12 may be removed by pulling the cap 12 axially with respect to the main body 11 as described below.

The device 10 comprises a cartridge 19 which is held in place by a cartridge holder 20. The cartridge holder 20 and cartridge 19 are connected and fixed relative to the main body 11 of the device 10. The cartridge 19 may be provided to a user separately to the device 10. The user may insert the cartridge 19 into the device 10.

The device 10 comprises a needle 17 which is held towards the proximal end thereof by a needle holder 18. The needle holder 18 comprises a cup shaped part 18a and a lip 18b.

The distal end of the needle 17 is contained within the tubular member 12a of the cap 12. The needle holder 18 which holds the needle 17 is axially movable relative to the main body 11 and the cartridge 19.

The cartridge 19 has a cartridge body 21, a neck 22 and a head 23. The head 23 is wider than the neck 22, thereby forming a flanged end. The neck 22 and head 23 contain a passage allowing medicament to pass therethrough as well as to receive the needle 17 once inserted. The head 23 is provided with a penetrable barrier such as a septum to close off the passage and to seal the contents of the medicament cartridge 19. The cartridge body 21, neck 22 and head 23 may be generally cylindrical in shape. However, alternative shapes may be employed. The cup-shaped portion 18a is shaped to engage with the head 23 of the cartridge 19. The cup-shaped portion 18a and head 23 may be dimensioned so as to provide a frictional fit when the cup-shaped portion 18a engages with the head 23. The needle holder 18 may also have a lip 18b to clip on to the head 23.

The cartridge holder 20 is generally tubular and is coaxial with respect to the main body 11. The main wall of the cartridge holder 20 extends around the body 21 of the cartridge 19 and extends towards the distal end of the device 10 so that it surrounds the head 23 of the cartridge 19, the needle holder 18 and a proximal end portion of the tubular member 12a of the cap 12. The cartridge holder 20 has a diameter greater than that of the cartridge 19 and needle holder 18. The cartridge holder 20 has ribs 24 extending inwardly from the main wall to support the cartridge 19 along the length of the cartridge 19. Alternatively, the cartridge holder 20 has a diameter approximately equal to that of the cartridge 19 so that a frictional fit is provided between the cartridge 19 and the cartridge holder 20 so that the ribs are not necessary. The cartridge holder 20 has a diameter approximately equal to that of the tubular member 12a so that a frictional fit is achieved when the cap 12 is attached to the rest of the device 10, as shown in FIG. 2A.

The cartridge holder 20 has a guide element 20a such as a pin extending from the inner surface of the main wall of the cartridge holder 20. The guide element 20a engages with a slotted link 12b which is a groove provided in the outer surface of the tubular member 12a of the cap 12. The slotted link 12b defines a path followed by the guide element 20a as the cap 12 is rotated by the user and as the cap is pulled away from the main body.

FIG. 2A shows a device 10 in accordance with one embodiment. In this embodiment, rotation of the cap leads to release of a compressed spring which, in turn, causes a needle holder to be displaced axially in a proximal direction towards the medicament cartridge.

A compressed spring 25 is provided inside the tubular member 12a. The compressed spring 25 may be a coil spring and fits around the distal end of the needle 17. Alternatively, a wave spring could be used. Wave springs provide lower work heights with the same force. The spring 25 is attached to the distal end of the cap 12 at one end thereof. The other end of the spring 25 is attached to a plate 26 provided at the proximal end of the tubular member 12a. The plate 26 is in abutment with the needle holder 18.

The outside surface of the curved wall of the tubular member 12a may be provided with a slotted link 12b. FIG. 2B shows a two-dimensional projection of the path defined by the slotted link 12b. The guide element 20a follows a circumferential path with no axial variation as the cap 12 is rotated from the position shown in FIGS. 2A and 2B to the position shown in FIGS. 3A and 3B with no axial displacement of the cap 12 with respect to the main body 11. In other words, the slotted link allows only rotary movement of the cap 12 during the stages shown in FIGS. 2 and 3. The axial portion of the slotted link 12b defines the path taken by the guide element 20a as the user pulls the cap 12 from the main body 11 subsequent to rotation of the cap 12 and the attachment of the needle holder 18 to the medicament cartridge 19. The slotted link 12b prevents detachment of the cap 12 before the cap has been rotated sufficiently to ensure attachment of the needle holder 18 to the medicament cartridge 19.

In alternative embodiments, the slotted link and guide element configuration may be provided between the cap 12 and the main body 11 or sleeve 13.

FIG. 3 shows the device 10 after the cap 12 has been rotated such that the spring 25 is released. The release of the spring is controlled by an activation element 27 located next to the plate 26. The activation element 27 can take any number of suitable forms. For example, the activation element 27 may be a block which holds the plate 26 and the spring 25 in place. In some embodiments, the plate 26 has an indent 28 along the circumference of the plate, as shown in FIG. 6A.

Figure 6B:
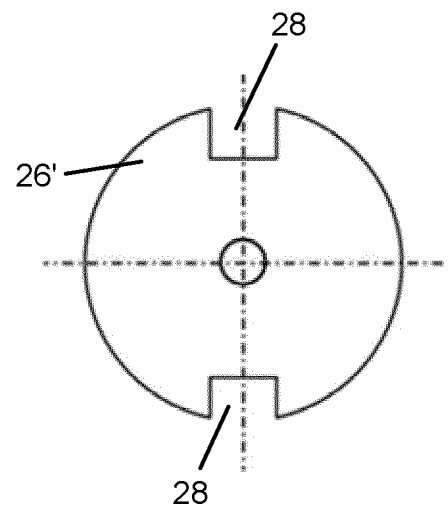

Alternatively, a plate 26' may be provided with two indents, as shown in FIG. 6B. In this alternative embodiment, the activation element 27 comprises two blocks.

As the cap 12 is rotated, the activation element 27 aligns with the indent or indents 28. The compressive force acting on the spring 25 is released. The plate 26 pushes the needle holder 18 and needle 17 in a proximal direction towards the medicament cartridge 19.

The proximal end of the needle 17 pierces the septum of the cartridge 19. The lip 18b provided around the inner surface of the cup shaped portion 18a clips onto the head 23. Further axial movement of the needle holder 18 is prevented by the lip 18b.

As stated above, in alternative embodiments, no lip is provided. The diameter of the cup shaped part 18a and the diameter of the head 23 of the medicament cartridge 19 can be arranged to ensure a close frictional fit between the needle holder 18 and the medicament cartridge 19.

As shown in FIG. 3B, the user needs to rotate the cap 12 by a preset amount before an axial movement of the cap 12 in the distal direction is possible.

As shown in FIGS. 4A and 4B, the cap 12 is rotated until the guide element 20a reaches the end of the circumferential portion of the slotted link 12b. The cap 12 can then be pulled away from the main body 11 in a distal direction. The guide element 20a follows the axially straight portion of the slotted link 12b.

FIG. 5A shows the device 10 as the cap 12 is separated from the rest of the device 10. The cap 12, spring 25 and plate 26 are pulled away from the rest of the device 10 in a distal direction. The needle holder 18 is left attached to the medicament cartridge 19 with the needle 17 inserted into the cartridge 19. The device 10 can then be used to commence the injection. The distal end of the device 10 is held against the patient's injection site and the device actuated.

In various embodiments, a mechanism may be provided to prevent unintended rotation of the cap. This serves as a safety mechanism, for example a child lock. In such embodiments, the user is required to push and rotate the cap at the same time.

The cap may be provided with an outer and an inner cap, whereby the outer cap needs to be pressed against inner cap to rotate it. Alternatively, the cap could be a cap with two lateral "buttons" which need to be pressed to overcome a stop ring.

Figure 7:
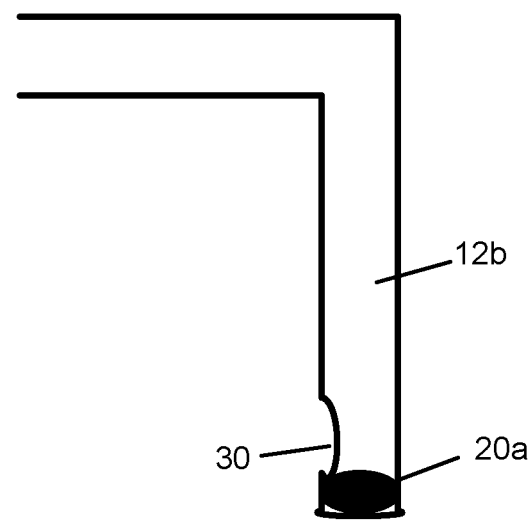
FIG. 7 shows a narrowing of a slotted link.

Alternatively, a narrowing 30 of the path 12b through which the guide element 20a passes may be provided, as shown in FIG. 7. The guide element requires a greater force to overcome this narrowing of the path.

In some embodiments, a second spring 80 may be provided that is configured to be released subsequent to further rotation of the cap 12 after the needle holder 18 is attached to the cartridge 19. The second spring 80 is arranged to push the cap 12 away from the main body 11 in a distal direction.

While the described embodiments relate to auto-injectors, it should be borne in mind that the subject matter can also be applied to other types of injection device such as syringes.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The term "drug delivery device" shall encompass any type of device or system configured to dispense a drug or medicament into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, microneedle), inhaler (e.g., nasal or pulmonary), an implantable device (e.g., drug- or API-coated stent, capsule), or a feeding system for the gastro-intestinal tract. The presently described drugs may be particularly useful with injection devices that include a needle, e.g., a hypodermic needle for example having a Gauge number of 24 or higher.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15$^{th}$ edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refer to any substance which is sufficiently structurally similar to the original substance so as to have substantially similar functionality or activity (e.g., therapeutic effectiveness). In particular, the term "analogue" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codable amino acids, or amino acids, including non-codable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®, Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')$_2$ fragments, which retain the ability to bind antigens. The antibody can be polyclonal, monoclonal, recombinant, chimeric, de-immunized or humanized, fully human, non-human, (e.g., murine), or single chain antibody. In some embodiments, the antibody has effector function and can fix a complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that can be useful include, for example, Fab fragments, F(ab')$_2$ fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

What is claimed is:

1. A medicament injection device comprising:
a main body;
a medicament cartridge holder fixed with respect to the main body, herein the medicament cartridge holder is configured to hold a medicament cartridge;
a needle carrier carrying a needle, wherein the needle carrier is axially movable with respect to the main body;
a rotatable cap at a distal end of the medicament injection device, wherein the cap comprises a first pre-stressed spring coupled to the needle carrier; and
at least one activation element configured to control the release of the first pre-stressed spring,
wherein the first pre-stressed spring is attached at a proximal end thereof to a plate, and wherein rotation of the cap from a first position in which the at least one activation element is in blocking engagement with the plate to a second position in which the at least one activation element is out of blocking engagement with the plate causes the plate and the first pre-stressed spring to be released, thereby causing the plate to push the needle carrier towards a proximal end of the medicament injection device.

2. The medicament injection device of claim 1, wherein the plate has at least one indent located along a circumferential surface thereof arranged to allow respective at least one activation element to pass therethrough when the at least one indent and the at least one activation element are in rotational alignment.

3. The medicament injection device of claim 1, further comprising a second pre-stressed spring arranged to be released in response to rotation of the cap subsequent to release of the first pre-stressed spring, thereby causing the cap to move axially away from the main body in a distal direction.

4. The medicament injection device of claim 1, wherein the cap comprises a tubular needle shielding element.

5. The medicament injection device of claim 1, further comprising a guide element and a cooperating groove, wherein one of the guide element and the cooperating groove is disposed in the cap and the other of the guide element and cooperating groove is disposed in a remainder of the medicament injection device so that the cap is prevented from being removed until the cap is rotationally aligned with the guide element.

6. The medicament injection device of claim 5, wherein the cap comprises a tubular needle shielding element and wherein the guide element depends on the medicament cartridge holder for engagement with the cap, and the cooperating groove is provided on an outer surface of the tubular needle shielding element to receive the guide element.

7. The medicament injection device of claim 5, wherein the cooperating groove comprises a circumferential part and an axial part.

8. The medicament injection device of claim 5, wherein the cooperating groove comprises a portion that is relatively narrow in comparison to a remainder of the cooperating groove.

9. The medicament injection device of claim 1, wherein the needle carrier is arranged to become fixed to the medicament cartridge.

10. The medicament injection device of claim 9, wherein the needle carrier comprises a lip arranged to cooperate with a head of the medicament cartridge.

11. The medicament injection device of claim 1, wherein the first pre-stressed spring is a helical spring or a wave spring.

12. The medicament injection device of claim 1, wherein the medicament cartridge holder contains a medicament cartridge having a penetrable barrier at a distal end thereof, and axial movement of the needle carrier towards the proximal end of the medicament injection device causes the needle to pierce the barrier of the medicament cartridge.

13. The medicament injection device of claim 12, wherein the medicament cartridge contains a medicament.

14. The medicament injection device of claim 1, wherein the at least one activation element is a block.

15. The medicament injection device of claim 1, wherein the medicament cartridge holder comprises a guide element and the cap comprises a cooperating groove, wherein the guide element is configured to follow a path of the cooperating groove.

16. The medicament injection device of claim 15, wherein the guide element is a protrusion extending from an inner surface of the medicament cartridge holder.

17. The medicament injection device of claim 15, wherein the guide element follows a circumferential portion of the path of the cooperating groove when the cap is rotated and the guide element follows an axial portion of the path of the cooperating groove when the cap is being removed from the medicament injection device.

18. The medicament injection device of claim 15, wherein the guide element follows an axial portion of the path of the cooperating groove subsequent to the needle piercing a barrier of the medicament cartridge.

19. A medicament injection device comprising:
a main body;
a medicament cartridge holder fixed with respect to the main body, wherein the medicament cartridge holder is configured to hold a medicament cartridge;
a needle carrier carrying a needle, wherein the needle carrier is axially movable with respect to the main body;
a rotatable cap at a distal end of the medicament injection device, wherein the cap comprises a first pre-stressed spring coupled to the needle carrier; and
at least one activation element,
wherein the first pre-stressed spring is attached at a proximal end thereof to a plate, and wherein rotation of the cap causes the plate and the first pre-stressed spring to be released, thereby causing the plate to push the needle carrier towards a proximal end of the medicament injection device,
wherein the plate has at least one indent located along a circumferential surface thereof arranged to allow respective at least one activation element to pass therethrough when the at least one indent and the at least one activation element are in rotational alignment.

20. A medicament injection device comprising:
a main body;
a medicament cartridge holder fixed with respect to the main body, wherein the medicament cartridge holder is configured to hold a medicament cartridge;
a needle carrier carrying a needle, wherein the needle carrier is axially movable with respect to the main body;
a rotatable cap at a distal end of the medicament injection device, wherein the cap comprises a first pre-stressed spring coupled to the needle carrier;
at least one activation element, and
a guide element and a cooperating groove, wherein one of the guide element and the cooperating groove is disposed in the cap and the other of the guide element and the cooperating groove is disposed in a remainder of the medicament injection device so that the cap is prevented from being removed until the cap is rotationally aligned with the guide element,
wherein the first pre-stressed spring is attached at a proximal end thereof to a plate, and wherein rotation of the cap causes the plate and the first pre-stressed spring to be released, thereby causing the plate to push the needle carrier towards a proximal end of the medicament injection device, and
wherein the cap comprises a tubular needle shielding element and wherein the guide element depends on the medicament cartridge holder for engagement with the cap, and the cooperating groove is provided on an outer surface of the tubular needle shielding element to receive the guide element.

* * * * *

UNITED STATES PATENT AND TRADEMARK OFFICE
CERTIFICATE OF CORRECTION

PATENT NO. : 10,918,804 B2
APPLICATION NO. : 15/778781
DATED : February 16, 2021
INVENTOR(S) : Marc Schader, Michael Helmer and Peter Nober Page 1 of 1

It is certified that error appears in the above-identified patent and that said Letters Patent is hereby corrected as shown below:

In the Claims

Column 11, Line 39, Claim 1, delete "herein" and insert -- wherein --

Column 12, Line 10, Claim 5, delete "and cooperating" and insert -- and the cooperating --

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*